United States Patent [19]

Dixon

[11] 4,215,090
[45] Jul. 29, 1980

[54] FLAME IONIZATION DETECTOR

[75] Inventor: Jack B. Dixon, Georgetown, Tex.

[73] Assignee: Purdue Research Foundation, West Lafayette, Ind.

[21] Appl. No.: 971,941

[22] Filed: Dec. 18, 1978

[51] Int. Cl.$^2$ .................... G01N 31/12; G01N 25/22; G01N 31/06
[52] U.S. Cl. .................... 422/54; 210/198 C; 422/70
[58] Field of Search ............ 422/54, 78, 70; 210/198 C, 31 C; 23/230 PC, 232 C, 232 E; 73/61.3

[56] References Cited

U.S. PATENT DOCUMENTS

| | | | |
|---|---|---|---|
| 2,991,158 | 7/1961 | Harley | 422/54 |
| 3,376,694 | 4/1968 | Owens et al. | 23/232 E |
| 3,451,780 | 6/1969 | Prescott et al. | 422/54 |
| 3,744,973 | 7/1973 | Dubsky | 422/54 |
| 3,753,654 | 8/1973 | Eggertsen | 422/54 |
| 3,767,363 | 10/1973 | Hofmann | 422/54 |
| 3,788,479 | 1/1974 | Szakasits | 422/78 |

Primary Examiner—R. E. Serwin
Attorney, Agent, or Firm—John R. Nesbitt

[57] ABSTRACT

A flame ionization detector is disclosed that is particularly useful for liquid chromatography. The detector is preferably utilized with a disc transport assembly with flame jets being positioned at opposite sides of the solute-bearing periphery of the disc. Hydrogen and air are injected through the flame jets and coaxial cables are connected to make electrical contact with the flame jets so that a flame ionization response occurs when organic compounds on the disc of the disc transport assembly are combusted in a potential field. When so combusted, a current is caused to flow from the flame jets through the coaxial cable to an electrometer where the current is amplified for display on a strip chart recorder or other output device.

15 Claims, 4 Drawing Figures

FLAME IONIZATION DETECTOR

FIELD OF THE INVENTION

This invention relates to a flame ionization detector and, more particularly, relates to a flame ionization detector that is particularly useful for a disc transport assembly for liquid chromatography.

BACKGROUND OF THE INVENTION

Liquid chromatograph detectors heretofore have usually been based on principles of detection that are compatible with the carrier solvent, such as the absorption of ultraviolet or visible light, fluorescence, and changes in refractive index. The detectors, however, have not been found to be compatible with all solvents and have been found to be either of fairly low sensitivity and/or sensitive to only certain types of compounds.

Various other types of detector systems have more recently been developed in an attempt to overcome at least some of these limitations. Of these systems, the so-called transport detectors have been found to present the greatest potential for meeting the needs of modern liquid chromatography, including the detection of polar pesticides.

With respect to the transport detectors, one of the more successful has utilized a disc for transporting the solute to be detected. Disc type transports are shown, for example, in K. Slais and M. Krejci, J. Chromatog. 91, 181(1974); R. P. W. Scott, C. G. Scott, M. Munroe and J. Hess, J. Chromatog. 99, 395 (1974); K. Aitzetmuller, J. Chromatog. Sci. 13, 454 (1975); T. Cotgrave, Chem. Ind. (London), 689 (1966); H. Dubsky, Chem, Listy 67, 533 (1973); E. G. Owens II, H. H. Gill, W. E. Hatton and J. G. Cobler, U.S. Pat. No. 3,376,694 (1968); and H. Dubsky, U.S. Pat. No. 3,744,973 (1973).

Flame ionization detectors have also been heretofore suggested and/or utilized in conjunction with liquid chromatography. Examples of flame ionization detectors are shown in E. Haahit and T. Nikkari, Acta. Chem. Scand. 17, 2565 (1963); J. E. Stouffer, T. E. Kersten and P. M. Krueger, Biochem. Biophys. Acta. 93, 191 (1964); A. Karmen, Anal. Chem. 38, 286 (1966); A. Karmen, Separation Sci. 2, 387 (1967); A. Karmen, Separation Sci. 2, 387 (1967); R. H. Stevens, J. Gas Chromatog. 6, 375 (1968); E. Foster and A. H. Weiss, J. Chromatog. Sci. 9, 266 (1971); S. Lieberman, U.S. Patent No. 3,128,619 (1964); H. W. Johnson Jr., E. E. Seibert and F. H. Stross, Anal. Chem. 40, 403 (1968); A. Karmen, L. D. Kane, M. Karasek and B. Lapidus, J. Chromatog. Sci. 8, 439 (1970); A. A. Balaukin, B. V. Vtorov, V. I. Kalmanovskii and V. P. Chernokozhin, U.S.S.R. Pat. No. 370,520 (1973); C. A. 79 (2), 603 (1973); E. G. Owens II, H. H. Gill, W. E. Hatton and J. G. Cobler, U.S. Pat. No. 3,376,694 (1968) and J. J. Szakasits, U.S. Pat. No. 3,788,479 (1974).

Use of a flame ionization detector in conjunction with a disc type transport assembly is shown again by way of example in U.S. Pat. No 3,788,479 (1974).

SUMMARY OF THE INVENTION

This invention provides an improved flame ionization detector that is particularly useful in conjunction with a disc type transport assembly for liquid chromatography. The detector includes a flame jet having an hydrogen-air flame directed to solute on the disc, the combustion of which in a potential field causes current to flow which is conducted to an electrometer before display.

It is therefore an object of this invention to provide an improved flame ionization detector.

It is another object of this invention to provide an improved flame ionization detector for liquid chromatography.

It is still another object of this invention to provide an improved flame ionization detector for liquid chromatography that is useful with a disc transport assembly.

It is yet another object of this invention to provide an improved flame ionization detector having flame jets with hydrogen-air flame directed to solutes to combust the same in a potential field.

It is still another object of this invention to provide an improved flame ionization detector having solutes combusted in a potential field to cause current flow to an electrometer for display.

With these and other objects in view, which will become apparent to one skilled in the art as the description proceeds, this invention resides in the novel construction, combination and arrangements of parts substantially as hereinafter described, and more particularly defined by the appended claims, it being understood that such changes in the precise embodiment of the hereindisclosed invention are meant to be included as come within the scope of the claims.

BRIEF DESCRIPTION OF THE DRAWINGS

The accompanying drawings illustrate a complete embodiment of the invention according to the best modes so far devised for the practical application of the principles thereof, and in which.

DESCRIPTION OF THE INVENTION

Figure 1:
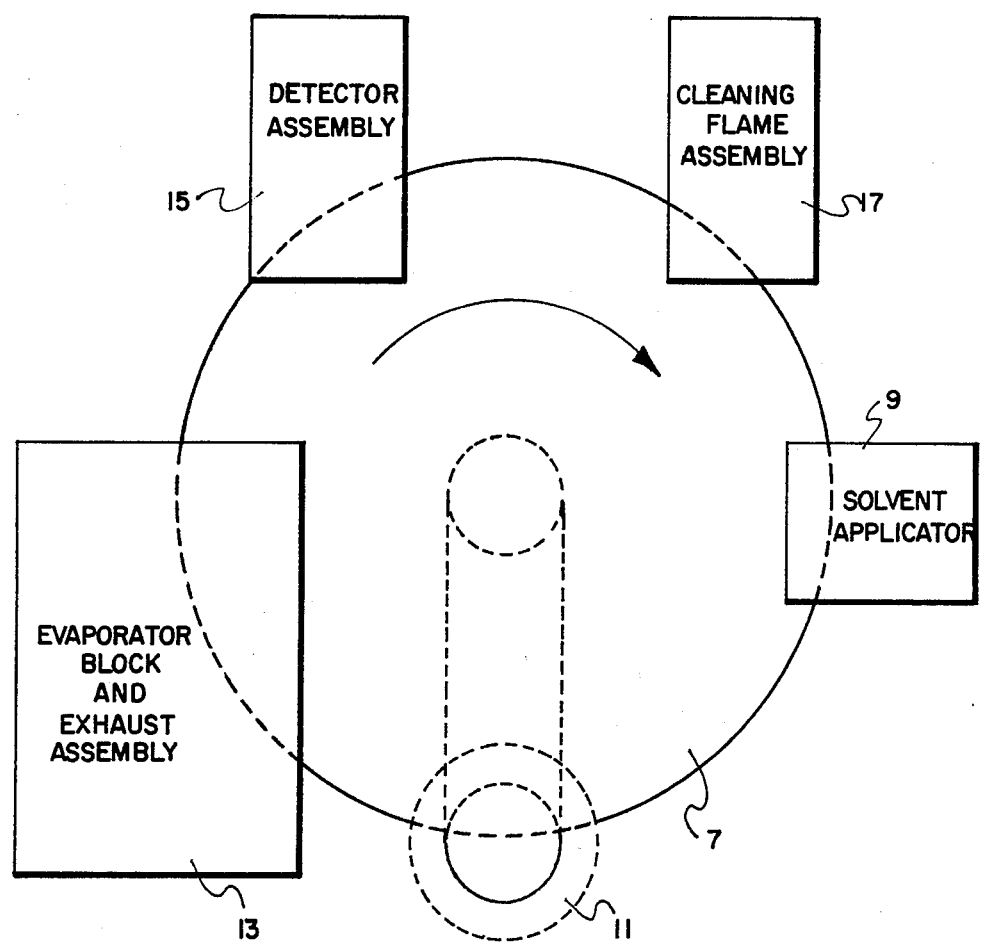
FIG. 1 is a block flow diagram of a typical disc type transport having flame ionization detection as taught in this invention associated therewith.

Referring now to the drawings, a flow diagram in block form of a typical disc type transport device is shown in FIG. 1. As shown, disc 7 is rotated with effluent being applied at the periphery of the disc by a solvent applicator 9, after which the disc is rotated by disc drive 11 so that the effluent is brought within evaporator block and exhaust assembly 13 where the solvent is volatilized by a warm stream of air and non-volatile solute then remains on the disc. The disc is then further rotated so that the solute is brought to the flame ionization detector assembly 15 of this invention. Finally, the disc is rotated to cleaning flame assembly 17 where the disc is flame cleaned to prepare the disc to receive additional effluent.

The disc type assembly may be as shown in U.S. Pat. No. 3,788,479 and hence has not been described in detail herein except to the extent necessary to illustrate the invention. The disc type assembly may also be a combination disc and quartz conveyor wherein a quartz belt is positioned at the periphery of the disc as taught and claimed in co-pending U.S. Patent Application entitled "Detection Unit with Solute Detector and Transport System" filed by Jack B. Dixon and Randall C. Hall, Ser. No. 970,324 filed Dec. 18, 1978 and assigned to the assignee of the present invention.

Figure 2:
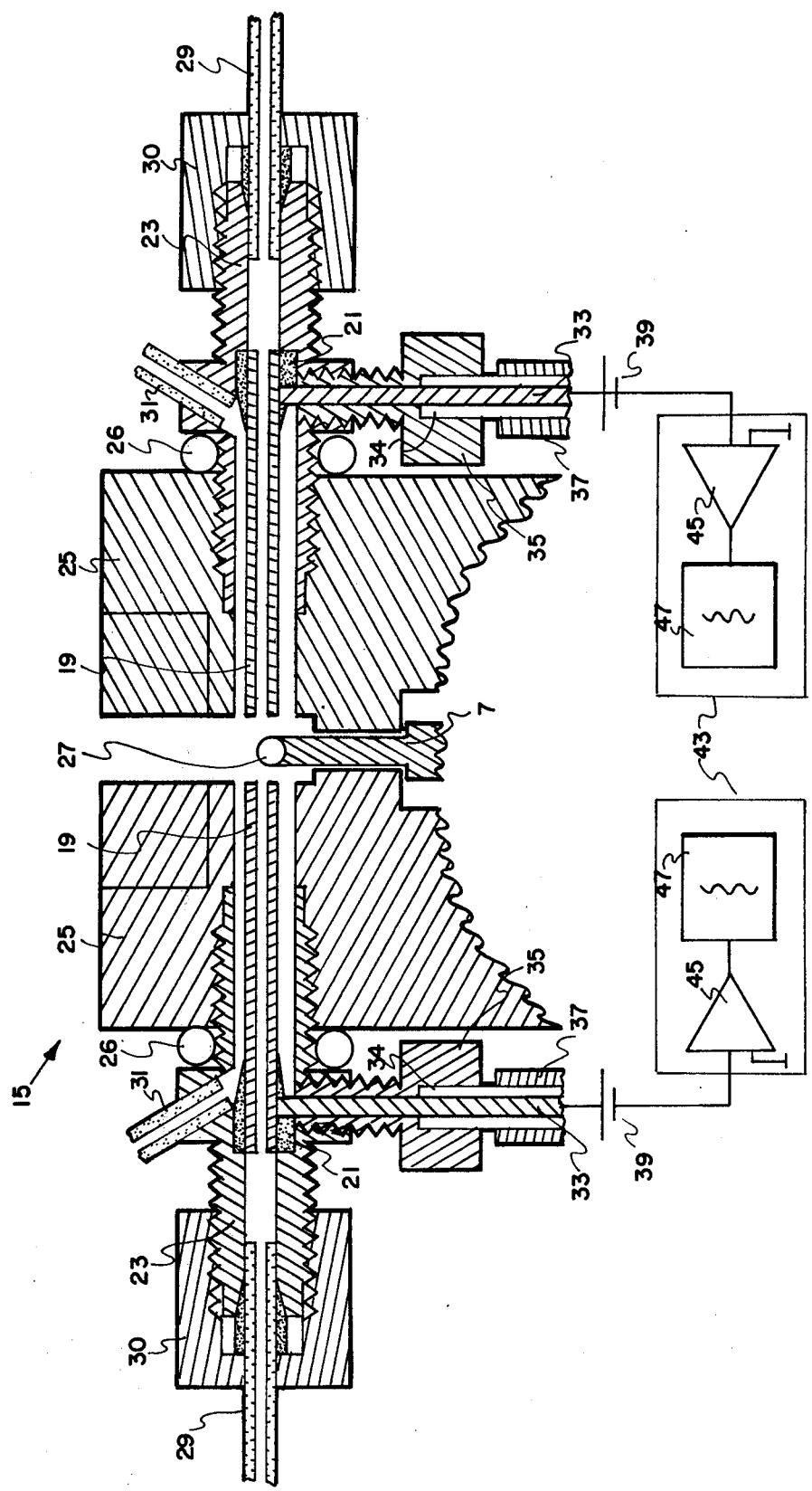
FIG. 2 is a cross-sectional view of the flame ionization detector of this invention.

The flame ionization detector 15 of this invention is shown in FIG. 2. As shown, the flame ionization detector includes a flame jet 19 (preferably of stainless steel) which is held in position by an insulator 21. The insulator 21 is pressed into the flame ionization detector (also called the "FID") housing 23 which is a modified Swagelok® union. Two FID housings are screwed into opposite tapped holes in the transport housing 25 (with O rings 26 thereat) such that the centers of the flame jets 19 are aligned with the periphery 27 of the disc conveyor 7. Air enters the FID housing 23 through tube 31 (which is affixed to FID housing 23) and sweeps the flame jets. Hydrogen enters the FID housing 23 through tube 29 (held in position by nut 30) and flows through the inside of the flame jets 19 to form two flames upon ignition.

Coaxial cable 33 makes electrical contact with the flame jets through holes in the insulators. The shield 34 of the coaxial cable 33 is soldered to cap screw 35 which enters threaded holes in the FID housing and has insulator 37 surrounding it at the portion leading from the device. As also indicated, cable 33 is connected with one side of a battery 39 the other side of which is connected with electrometer 45, which is connected to a strip chart recorder 47. Although separate batteries and electrometers are shown in FIG. 2, both sides of detector 15 could be connected with a single battery and electrometer, if desired.

A normal flame ionization response occurs when organic compounds are combusted in a potential field. An air-hydrogen flame is used to support combustion due to its low background current and favorable temperature.

In operation under normal conditions, the potential field is obtained by grounding the transport housings 25, thus grounding the transport disc 7, and placing battery 39 (22–300 volts) in series between each flame jet 19 and electrometer 45. Thus, when solute on the periphery of the disc conveyor is combusted in the air-hydrogen flame, a current flows from the flame jets through the coaxial cable 33 and through the battery 39 to the electrometer 45 where the electrical current is amplified by electrometer 45 and then displayed on strip chart recorder 47.

Typical gas flow rates are 30 ml/min hydrogen per flame jet and 200 ml/min air per flame jet.

Figure 4:
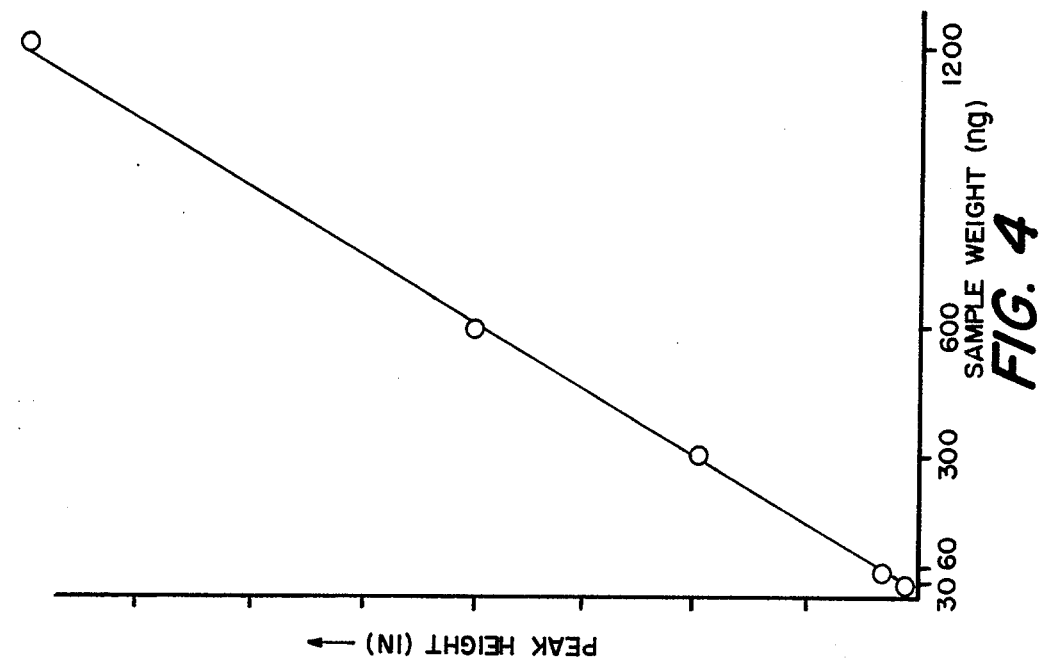
FIG. 4 is a graph illustrating linearity of response of the flame ionization detector of this invention.
Figure 3:
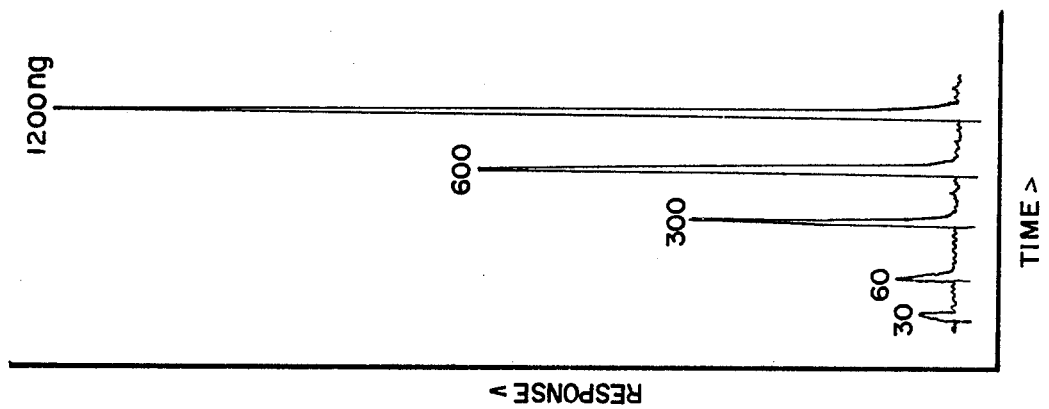
FIG. 3 is a graph of detector response to tetradecane.

Detector sensitivity and linearity of response for the flame ionization detector were determined for tetradecane using a 300 μl sample loop to simulate a chromatographic peak. Hexane was used as the solvent and was applied to the transport conveyor at 1.33 ml/min as the transport disc was rotated at 4 rpm. the transport housing was heated to 120° C. Detector response to quantities of tetradecane from 30 ng to 1.2 μg is shown in FIG. 3. As can be determined from FIG. 3, the minimum detectable quantity is approximately 15 ng tetradecane. Linearity of the response is shown by the graph of FIG. 4.

As can be appreciated from the foregoing, this invention provides an improved flame ionization detector that is particularly useful with the disc type transport assembly for liquid chromatography.

What is claimed is:

1. A flame ionization detector for a liquid chromatography device having a transport disc within a transport housing with the peripheral portion of the disc being adapted to carry eluents to be detected, said detector comprising:
   flame jet means for applying a flame jet toward said peripheral portion of said transport disc within said transport housing at a detection area; and
   electrical means connected with said flame jet means to cause current flow through said flame jet for detecting the flame ionization response when compounds to be detected are carried by said disc within said detection area.

2. The detector of claim 1 wherein said flame jet means includes a tube one end of which is substantially aligned with said peripheral portion of said disc at said detection area, said tube having openings to receive a fluid at a point spaced from said one end.

3. The detector of claim 2 wherein said detector includes a detector housing for mounting said tube on said transport housing with said tube being substantially normal to the plane of said disc within said transport housing.

4. The detector of claim 3 wherein said tube and said transport housing and disc are electrically conductive, and wherein said detector housing provides an electrical insulator with respect to said tube and said transport housing and disc.

5. The detector of claim 4 wherein said electrical means are connected with said tube and transport housing and disc to provide a potential field at said detection area.

6. The detector of claim 1 wherein said electrical means includes electrometer means.

7. The device of claim 6 wherein said electrometer means includes an amplifier and wherein said electrical means includes a battery connected with said electrometer means.

8. A flame ionization detector, comprising:
   flame jet means including a tube adapted to receive a fluid for supplying a flame jet at one end of said tube to a detection area; and
   electrical means connected with said flame jet means to cause current flow through said flame jet for providing an electrical signal indicative of detected compounds sensed at said detection area while said flame jet is supplied thereto by said flame jet means.

9. The detector of claim 8 wherein said electrical means establishes a potential field at said detection area.

10. The detector of claim 9 wherein said electrical means includes an electrometer and a battery connected with said flame jet to cause current flow due to flame ionization response.

11. A flame ionization detector for a liquid chromatography device having an electrically conductive disc within an electrically conductive transport housing with the peripheral portion of the disc being adapted to carry eluents to be detected, said detector comprising:
   flame jet means including an electrically conductive tube having an end portion from which a flame jet is outwardly directed when said flame jet means is operating, and inlets adapted to receive hydrogen and air for enabling establishment of said flame jet;
   flame jet mounting means for mounting said flame jet means in said transport housing so that said tube is insulated from said transport housing and transport disc, said tube extending through said transport housing with said end portions being adjacent to the periphery of said disc within said transport housing;

an electrometer;

a battery connected in series with said electrometer; and a coaxial cable electrically connected at one end to said tube and to said transport housing and disc and at the other end with said battery whereby a potential field is established between said tube and said disc so that a flame ionization response occurs when organic compounds are combusted in said potential field to cause current flow through said flame jet, coaxial cable and battery to said electrometer.

12. The device of claim 11 wherein air supplied to said tube sweeps said flame jet.

13. The detector of claim 11 wherein said flame jet means includes a pair of flame jet units which are mounted in opposite sides of said housing with said tubes being aligned and having said peripheral portion of said transport disc therebetween.

14. The detector of claim 11 wherein said inner conductor of said coaxial cable is connected with said tube and said outer conductor is grounded as are said transport housing and transport disc.

15. The detector of claim 11 wherein said electrometer includes an amplifier and a strip chart recorder for recording detected responses.

* * * * *